(12) United States Patent
Beveridge et al.

(10) Patent No.: US 11,544,844 B2
(45) Date of Patent: Jan. 3, 2023

(54) MEDICAL IMAGE PROCESSING METHOD AND APPARATUS

(71) Applicant: Canon Medical Systems Corporation, Otawara (JP)

(72) Inventors: Erin Beveridge, Edinburgh (GB); Paul Thomson, Edinburgh (GB); Brian Mohr, Edinburgh (GB); Georgios Diakidis, Edinburgh (GB); Naotaka Sakashita, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 199 days.

(21) Appl. No.: 16/916,242

(22) Filed: Jun. 30, 2020

(65) Prior Publication Data

US 2021/0027460 A1    Jan. 28, 2021

Related U.S. Application Data

(63) Continuation-in-part of application No. 16/522,060, filed on Jul. 25, 2019, now abandoned.

(30) Foreign Application Priority Data

May 29, 2020    (JP) .............................. JP2020-094447

(51) Int. Cl.
  *G06T 7/00*    (2017.01)
  *G16H 30/40*   (2018.01)

(52) U.S. Cl.
  CPC ........... *G06T 7/0012* (2013.01); *G16H 30/40* (2018.01); *G06T 2207/20081* (2013.01); *G06T 2207/30016* (2013.01)

(58) Field of Classification Search
  CPC ......... G06T 7/0012; G06T 2207/20081; G06T 2207/30016; G16H 30/40
  See application file for complete search history.

(56) References Cited

U.S. PATENT DOCUMENTS

| 9,159,127 | B2 | 10/2015 | Meetz et al. | |
| 2004/0267153 | A1* | 12/2004 | Bergethon | A61B 5/4076 600/554 |
| 2017/0367633 | A1 | 12/2017 | Samadani | |

(Continued)

FOREIGN PATENT DOCUMENTS

WO    WO 2017/106645 A1    6/2017

OTHER PUBLICATIONS

Brainomix, e-aspects, https://brainomix.com/e-aspects ,retrieved on May 20, 2019, 9 pages.

(Continued)

*Primary Examiner* — Vu Le
*Assistant Examiner* — Julius Chai
(74) *Attorney, Agent, or Firm* — Oblon, McClelland, Maier & Neustadt, L.L.P.

(57) ABSTRACT

A medical image processing apparatus comprises processing circuitry configured to: obtain image data representative of a brain of a subject; obtain data representing a clinical sign or symptom of the subject, wherein the clinical sign or symptom is relevant to a brain condition; process the image data to obtain an estimation of an abnormality in the brain of the subject; and determine whether the estimation of the abnormality is consistent with the data representing the clinical sign or symptom.

23 Claims, 6 Drawing Sheets

(56) References Cited

U.S. PATENT DOCUMENTS

| | | |
|---|---|---|
| 2018/0365824 A1 | 12/2018 | Yuh et al. |
| 2019/0046124 A1* | 2/2019 | Samadani |
| 2019/0192089 A1* | 6/2019 | Maresky .............. A61B 6/5217 |
| 2022/0044821 A1* | 2/2022 | Eichler ................. G16H 50/70 |

OTHER PUBLICATIONS

Kobayashi, M., "Horizontal gaze deviation on computed tomography: the visual criterion and lesion characteristics in ischemic stroke", Acta Neurologica Belgia, May 20, 2018, 7 pages.

Spokoyny, I, et al., "Visual Determination of Conjugate Eye Deviation on Computed Tomography Scan Predicts Diagnosis of Stroke Code Patients", Journal of Stroke and Cerebrovascular Diseases, vol. 25, No. 12, pp. 2809-2813.

Girshick, R, et al., "Rich feature hierarchies for accurate object detection and semantic segmentation", The IEEE Conference on Computer Vision and Pattern Recognition (CVPR), Jun. 2014, 8 pages.

National Institutes of Health Stroke Scale/Score (NIHSS), https://www.mdcalc.com/nih-stroke-scale-scores-nihss, 7 pages.

Prevost's Sign, https://radiopaedia.org/articles/prevost-sign-eyes?lang=qb, 5 pages.

\* cited by examiner

MEDICAL IMAGE PROCESSING METHOD AND APPARATUS

CROSS-REFERENCE TO RELATED APPLICATIONS

This application is a Continuation-in-Part Application of U.S. patent application Ser. No. 16/522,060, filed Jul. 25, 2019 and based upon and claiming the benefit of priority from Japanese Patent Application No. 2020-094447, filed May 29, 2020, the entire contents of all of which are incorporated herein by reference.

FIELD

Embodiments described herein relate generally to a method and apparatus for processing medical images to obtain information about an abnormality, and comparing the information obtained to information about a clinical sign or symptom.

BACKGROUND

It is known for clinicians to review a scan of a patient's brain to look for signs that a stroke has occurred, for example an ischemic stroke. The scan may be a non-contrast computed tomography (NCCT) scan. Reading a NCCT scan to look for signs of ischemic stroke can be particularly challenging due to the subtle nature of the imaging findings. For example, finding a region of ischemia may involve detecting very subtle differences in image contrast.

A clinician's interpretation of findings in imaging may in some circumstances be weighted by a clinical picture that they have of the patient. For example, if the clinician has already examined the patient, the clinician may know a side of the patient (right or left) on which symptoms have presented. However, such clinical information may not always be readily available, or at least not immediately presentable to the clinician at time of reviewing the imaging.

Patients who have had a stroke often have had previous strokes or have small vessel disease. Imaging features resulting from the previous strokes and/or small vessel disease may confound the task of discerning the imaging features specific to the current acute episode. It may be difficult to distinguish signs of a previous stroke from signs of a recent stroke.

BRIEF DESCRIPTION OF THE DRAWINGS

Embodiments are now described, by way of non-limiting example, and are illustrated in the following figures, in which.

DETAILED DESCRIPTION

Certain embodiments provide a medical image processing apparatus comprising processing circuitry configured to obtain image data representative of a brain of a subject; obtain data representing a clinical sign or symptom of the subject, wherein the clinical sign or symptom is relevant to a brain condition; process the image data to obtain an estimation of an abnormality in the brain of the subject; and determine whether the estimation of the abnormality is consistent with the data representing the clinical sign or symptom.

Certain embodiments provide a medical image processing method comprising: obtaining image data representative of a brain of a subject; obtaining data representing a clinical sign or symptom of the subject, wherein the clinical sign or symptom is relevant to a brain condition; processing the image data to obtain an estimation of an abnormality in the brain of the subject; and determining whether the estimation of the abnormality is consistent with the data representing the clinical sign or symptom.

Figure 1:
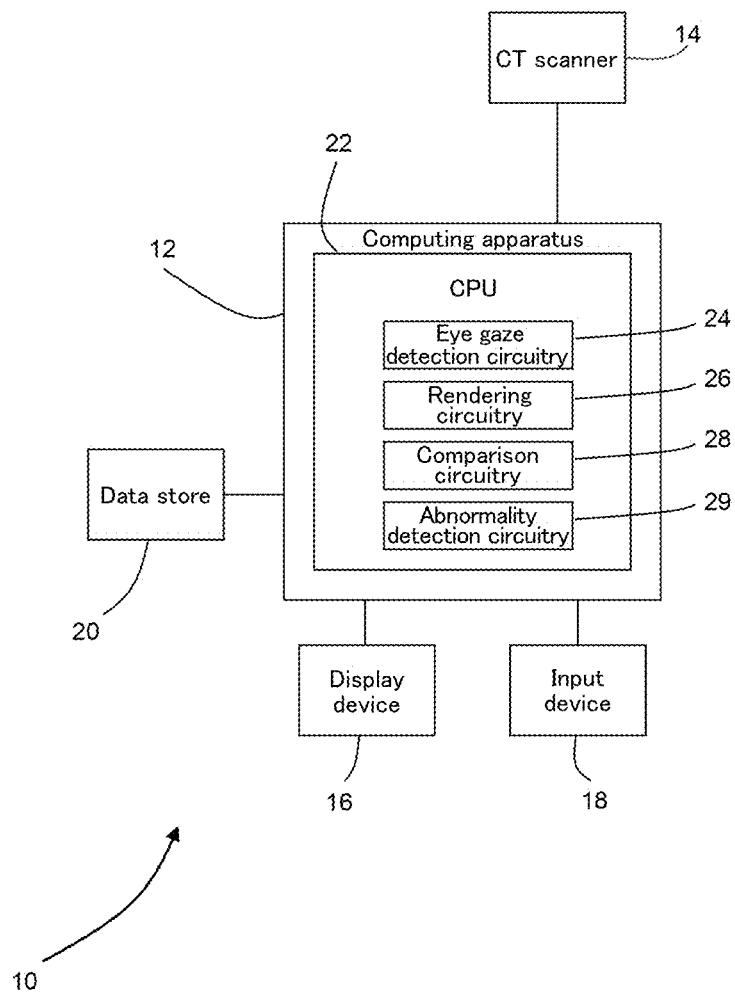
FIG. 1 is a schematic diagram of an apparatus according to an embodiment.

A medical image processing apparatus 10 according to an embodiment is illustrated schematically in FIG. 1. The medical image processing apparatus 10 is configured to process and display medical images of a patient or other subject.

The medical image processing apparatus 10 comprises a computing apparatus 12, which in this case is a personal computer (PC) or workstation. The computing apparatus 12 is connected to a display device 16, for example a screen, and an input device or devices 18, such as a computer keyboard and mouse. In some embodiments, the display device 16 is a touch screen, which also acts as an input device 18. The computing apparatus 12 is connected to a data store 20.

The medical image processing apparatus 10 is connected to a CT scanner 14 which is configured to perform a non-contrast CT scan (NCCT) scan of a patient or other subject to obtain volumetric medical imaging data. In the present embodiment, the scan is a scan of the brain. In other embodiments, any suitable body part may be scanned.

In alternative embodiments, data may be obtained using any suitable modality and/or acquisition technique. The CT scanner 14 may be replaced or supplemented by one or more scanners configured to obtain two-dimensional or three-dimensional imaging data in any suitable imaging modality, for example a CT scanner, cone-beam CT scanner, MRI (magnetic resonance imaging) scanner, X-ray scanner, ultrasound scanner, PET scanner (positron emission tomography) or SPECT (single photon emission computed tomography) scanner.

Data obtained using the CT scanner 14 is stored in data store 20 and supplied to the computing apparatus 12. In other embodiments, the computing apparatus 12 may obtain the data directly from the CT scanner 14. In alternative embodiments, the medical image processing apparatus 10 receives medical imaging data and/or medical images from one or more further data stores (not shown) instead of or in addition to data store 20. For example, the medical image processing apparatus 10 may receive medical imaging data from one or more remote data stores which may form part of a Picture Archiving and Communication System (PACS) or other information system, for example a laboratory data archive, an Electronic Medical Record (EMR) system, or an Admission Discharge and Transfer (ADT) system.

Computing apparatus 12 provides a processing resource for automatically or semi-automatically processing medical imaging data. Computing apparatus 12 comprises a central processing unit (CPU) 22.

The computing apparatus 12 provides a processing resource for automatically or semi-automatically processing data sets. In the present embodiment, the data sets comprise medical imaging data. For simplicity, we will refer below to the processing and retrieval of medical images. However, operations described below as being performed on medical images may in practice be performed on any suitable sets of imaging data that are representative of medical images. In some circumstances, imaging data may be processed internally by the computing apparatus 12 without any corresponding image being displayed.

The computing apparatus 12 includes eye gaze detection circuitry 24 configured to determine a direction of eye gaze; rendering circuitry 26 configured to render images from imaging data; comparison circuitry 28 configured to compare data to detect inconsistencies, for example to detect an inconsistency between an eye gaze determined from imaging data and an eye gaze determined by a different method; and abnormality detection circuitry 29 configured to process imaging data to identify abnormalities, for example to detect regions of ischemia and/or hyperdense vessels.

In the present embodiment, the circuitries 24, 26, 28, 29 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays). In the present embodiment, the circuitries 24, 26, 28, 29 are each implemented as part of the CPU 22. In alternative embodiments, the circuitries 24, 26, 28, 29 may be implemented separately or form part of two or more CPUs. In further embodiments, at least part of the method may be performed on one or more Graphical Processing Units (GPUs).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
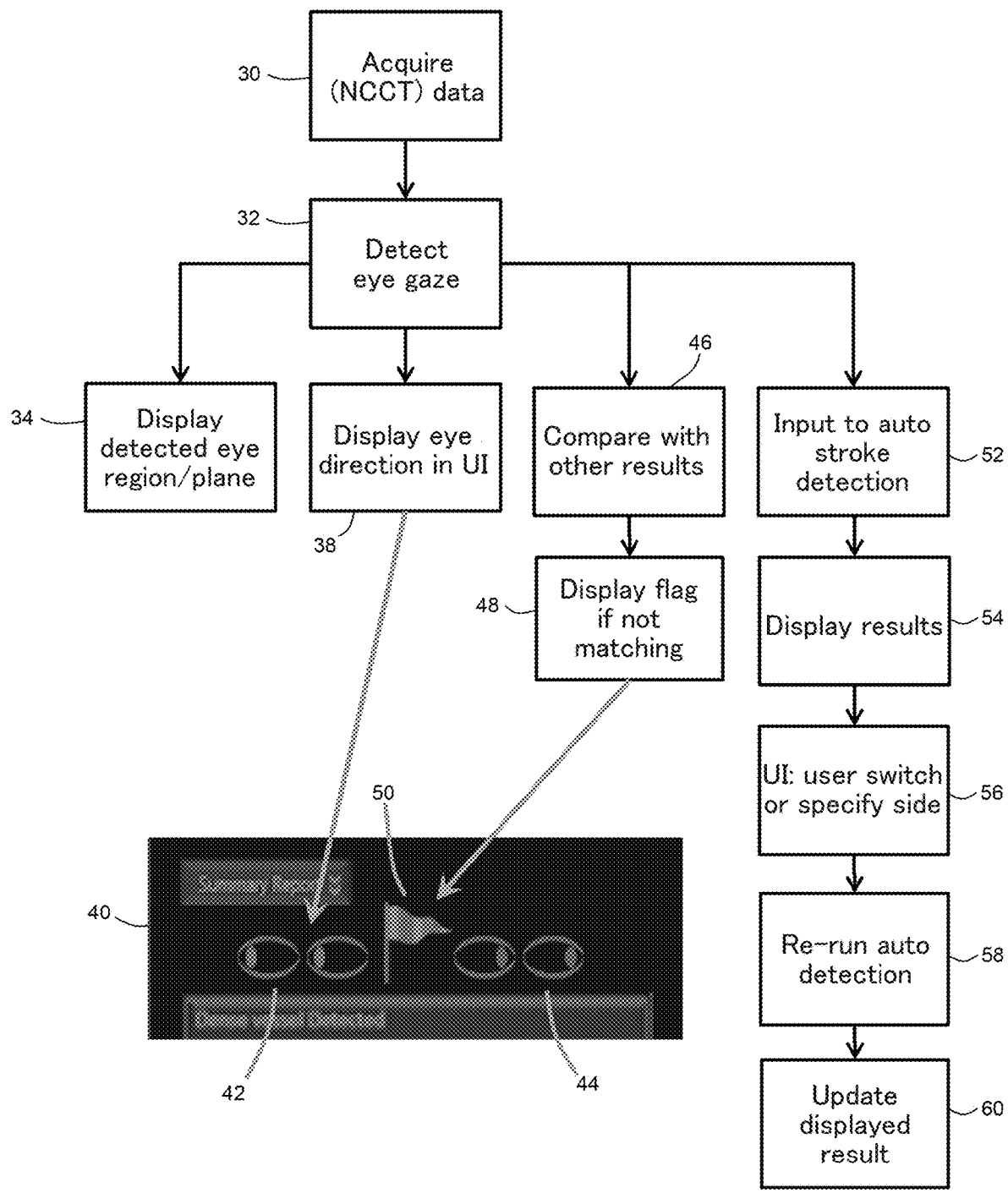
FIG. 2 is a flow chart illustrating in overview a method of an embodiment.

The system of FIG. 1 is configured to perform a series of stages as illustrated in overview in the flow chart of FIG. 2.

At stage 30, the CT scanner acquires a non-contrast CT scan of the brain of a patient who is suspected to have had a stroke. Volumetric data from the NCCT scan is passed to the data store 20, and from the data store 20 to the eye gaze detection circuitry 24. In other embodiments, the eye gaze detection circuitry 24 may obtain a set of volumetric NCCT data from any suitable data store. The NCCT data may be obtained by the eye gaze detection circuitry 24 at any suitable time after the NCCT scan has been obtained.

At stage 32, the eye gaze detection circuitry 24 processes the NCCT scan data to obtain an estimate of a direction of gaze of the patient's eyes. References to eyes below refer to the globes, which may also be called the eyeballs. It is expected that both eyes are looking in the same direction. In the present embodiment, the eye gaze detection circuitry 24 outputs a classification into one of three classes. In a first class, the direction of gaze is to the right. In a second class, the direction of the gaze is to the left. In a third class, either the direction of gaze is to neither left or right, or the direction of gaze is unknown. The classifications will be referred to below as Right, Left, and Neither/Unknown.

An angle of gaze of the eyes may be defined relative to the contralateral plane of the patient's skull. An angle of gaze may be defined as described in, for example, Kobayashi, M., Horizontal gaze deviation on computed tomography: the visual criterion and lesion characteristics in ischemic stroke. Acta Neurol Belg (2018) 118: 581. https://doi.org/10.1007/s13760-018-0949-1 or Spokoyny, Ilana et al., Visual Determination of Conjugate Eye Deviation on Computed Tomography Scan Predicts Diagnosis of Stroke Code Patients, Journal of Stroke and Cerebrovascular Diseases, Volume 25, Issue 12, 2809-2813.

In some embodiments, the eye gaze detection circuitry 24 may return an angle of eye gaze, for example as a numerical value. The angle of eye gaze may be returned in addition to, or instead of, the determination that the direction of eye gaze is Left, Right, or Neither/Unknown.

In the present embodiment, a trained model is used to determine whether the eyes are biased to the right, to the left, or neither/unknown. The trained model may be a deep learning classifier. For example, an R-CNN (regions with convolutional neural network features) method may be used, which may be similar to that described in R. Girshick, J. Donahue, T. Darrell, J. Malik, "Rich feature hierarchies for accurate object detection and semantic segmentation", The IEEE Conference on Computer Vision and Pattern Recognition (CVPR), June 2014.

In other embodiments, any suitable method may be used to determine whether the direction of eye gaze is Left, Right, or Neither/Unknown. In further embodiments, any suitable classification of eye gaze direction may be used.

In the present embodiment, an aim of training the trained model is that the trained model will be 100% specific, or as close as possible to 100% specific. If Right is predicted, the eyes will always be looking right. If Left is predicted, the eyes will be looking left. Any uncertainty in the determination of the eye gaze will lead to the Neither/Unknown classification.

In some circumstances, the scan of the brain may have be obtained such as to exclude the patient's eyes from the anatomical region scanned using the CT scanner. In at least some such cases, it may be possible to obtain a direction of eye gaze based on other anatomy. In some embodiments, a trained model may output a classification based on anatomy other than the globes. For example, the trained model may be trained to take into account the extraocular muscles. A compression of the extraocular muscles may be indicative of an eye gaze direction. In other embodiments, the determining of the direction of eye gaze may be based on segmenting the extraocular muscles in the NCCT scan.

The determined direction of eye gaze indicates whether the eyes are turned to the patient's right or to the patient's left, relative to the patient's skull. The eye gaze detection circuitry 24 outputs a direction of the eye gaze as one of three classifications: Right, Left, or Neither/Unknown.

In some embodiments, the eye gaze detection circuitry 24 may also output an angle of eye gaze. In further embodiments, a respective eye gaze direction and/or angle may be determined individually for each of the patient's eyes. In some embodiments, an eye gaze angle is compared to a threshold angle, and the eye gaze direction is only reported as right or left if the eye gaze angle exceeds the threshold angle.

In the present embodiment, the eye gaze detection circuitry 24 obtains the eye gaze direction automatically by processing the volumetric NCCT data. In other embodiments, a direction of eye gaze may be provided by a clinician based on clinical observation of the patient. In further embodiments, a clinician may analyze the volumetric NCCT data manually to determine a direction of eye gaze. The clinician may input the direction of eye gaze into the computing apparatus 12 using the input device 18.

In clinical practice, clinical gaze deviation of the eyes is well documented as a symptom of stroke. Clinical deviation of the eyes is called Prevost's sign. Gaze deviation is defined as equal sustained deviation of both globes from a midline position towards the same side. If present, the eyes deviate to the side of the hemisphere of the brain that has been damaged by stroke. The damaged hemisphere is opposite to the side of the body in which symptoms present, for example paralysis or facial drooping.

Conjugate eye deviation on the CT scan is an imaging feature which is highly specific for the clinical symptom of eye gaze. In some circumstances, eye gaze as determined from the CT scan may be used as a substitute for a clinical symptom that is obtained by examination of the patient.

Gaze deviation of the eyes due to stroke is generally a result of damage to the frontal eye fields, a cortical area in the caudal part of the midline frontal gyrus or its corticopontine projections.

Gaze deviation has been found to occur in approximately 20% to 30% of patients with cerebral hemispheric stroke. Gaze deviation has low sensitivity but has high specificity and has been shown to have a Positive Predictive Value of 93% for reliably lateralizing to the ischemic hemisphere.

It has been shown that when a clinician identifies eye deviation they are sensitised to ischemic changes in the corresponding hemisphere, particularly in the absence of clinical information.

After stage 32, the flow chart proceeds to any or all of four possible stages 34, 38, 46, 52 which may be performed simultaneously or may be performed sequentially in any order.

At stage 34, the rendering circuitry 26 receives from the eye gaze detection circuitry 24 an indication of an eye region within the volumetric NCCT data. For example, the eye region may be indicated by a bounding box obtained from segmentation. The rendering circuitry 26 renders from the volumetric NCCT data an image showing the eye region. The rendering circuitry 26 displays the rendered image of the eye region on the display screen 16. The rendered image may provide a quick view of eye gaze. The rendered image may be displayed on any suitable user interface. For example, the rendered image may be displayed on a clinical dashboard that a user can use to review images and/or other medical data.

A user, for example a clinician, views the displayed image of the eye region. By viewing the image, the user may manually verify that the automated detection of eye gaze is correct.

In the present embodiment, the rendered image is representative of a portion of an axial slice. The axial slice is a slice through the head which passes through the lenses of the eyes. The user may view the entire axial slice by clicking on the displayed portion. In other embodiments, any suitable image of the eye region may be displayed.

At stage 38, the rendering circuitry 26 displays on display screen 16 a simplified representation 40 of the eye gaze. The simplified representation of eye gaze may be described as a cartoon. The simplified representation 40 may be displayed on the same user interface as the rendered image. The simplified representation 40 is intended to provide a basic indication of whether the deviation of the eyes is to the left or to the right.

In the present embodiment, the representation 40 comprises a first line drawing 42 of a pair of eyes looking to the left and a second line drawing 44 of a pair of eyes looking to the right. The rendering circuitry 26 highlights either the first line drawing 42 (as shown in FIG. 2) or the second line drawing 44 in accordance with the determination of eye gaze direction as left or right as received from the eye gaze detection circuitry 24.

The representation 40 may provide a simple way for the user to view the determined eye gaze direction at a glance.

In some embodiments, the representation 40 may be displayed without displaying the rendered image. For example, the representation 40 may be displayed as part of a clinical summary.

At stage 46, the comparison circuitry 28 compares the eye gaze direction that was determined at stage 32 to at least one other result. The other result or results comprise further data that may be relevant to the laterality of stroke. The other result or results may include, for example, at least one symptom that has been manually input by a user, for example a clinician. For example, the symptom may be one-sided facial drooping or one-sided paralysis. The symptom may be one of the left- or right-sided indicators listed in the National Institutes of Health Stroke Scale/Score (NIHSS).

The comparison circuitry 28 outputs a determination of whether the eye gaze direction that was determined at stage 32 is consistent with the at least one other result. If the eye gaze direction is not consistent with the at least one other result, the flow chart proceeds to stage 48. At stage 48, the rendering circuitry 26 displays reference information to the user that alerts the user to the inconsistency. In the present embodiment, the reference information comprises a flag 50 on the display screen 16, for example on the representation 40. In the embodiment of FIG. 2, the eye gaze is shown as a finding, with a flag 50 included if there is a mismatch. In other embodiments, any suitable display of reference information may be used. The reference information may provide a warning to the user that an inconsistency has been detected.

At stage 52, the eye gaze detection circuitry 24 passes the eye gaze direction to the abnormality detection circuitry 29. The abnormality detection circuitry 29 uses the eye gaze direction as an input to an abnormality detection procedure. In further embodiments, any suitable information derived from imaging and/or any information relating to any suitable clinical symptom may be used as an input to the abnormality detection procedure.

The abnormality detection procedure may also be described as an automated stroke detection. The abnormality detection procedure comprises processing the volumetric NCCT data received at stage 30 to identify at least one type of abnormality in the NCCT scan.

In other embodiments, an eye gaze direction and/or eye gaze angle may be determined as part of the abnormality detection procedure.

In the embodiment of FIG. 2, the abnormality detection procedure of stage 52 is performed on imaging data that is representative of the entire brain. The abnormality detection circuitry 29 is configured to detect regions of ischemia and regions of hyperdense vessels in the brain. The abnormality detection circuitry 29 outputs one or more regions that have been identified as regions of ischemia or regions of hyperdense vessels. In other embodiments, the abnormality detection circuitry 29 may be configured to detect any appropriate brain abnormality.

At stage 54, the rendering circuitry 26 renders at least one image using the results of the abnormality detection procedure and displays the at least one image (not shown in FIG. 2) on display screen 16. In the present embodiment, the at least one image is displayed as part of the same user interface as the eye image and the representation 40. At least one identified region of ischemia and/or hyperdense vessels is highlighted in the at least one image.

In other embodiments, the rendering circuitry 26 may represent the results of the abnormality detection procedure using any suitable display method. For example, the rendering circuitry 26 may display text indicating whether or not any abnormality has been detected. The rendering circuitry 26 may label regions of a displayed image.

In the present embodiment, the abnormality detection circuitry 29 outputs a determination of a side of the brain on which all or most abnormal regions have been detected. The rendering circuitry 26 may display an indication (for example, a text display or visual display) that indicates the side of the brain on which all or most abnormal regions have been found.

The comparison circuitry 28 compares the side of the brain output by the abnormality detection circuitry 29 at stage 52 to the direction of eye gaze determined at stage 32. If the side of the brain output by the abnormality detection circuitry 29 is inconsistent with the eye gaze determined at stage 32, the rendering circuitry 26 displays the flag 50 or a further flag to indicate that an inconsistency is present.

In other embodiments, the abnormality detection procedure may exclude results from a side of the brain that does not correspond to the determined eye gaze direction.

At stage 56, a user of the user interface (for example, a clinician) specifies a side of the brain on which to run the abnormality detection procedure.

The user may specify the side of the brain based on the eye gaze direction determined at stage 32. For example, if the eye gaze is looking to the left, this is indicative that the left side of the brain is damaged. This is the opposite side on which symptoms occur. For example, damage to the left side of the brain may result in drooping or paralysis on the right side of the body.

If the eye gaze is looking to the left, the user may specify performing an abnormality detection only on the left side of the brain. When deciding on the side, the user may take into consideration whether the eye gaze has been found to be inconsistent with other information (for example, an inconsistency as shown to the user by flag 50 or by a further flag).

At stage 58, the abnormality detection circuitry 29 re-runs the abnormality detection procedure to detect stroke signs on the side of the brain that is specified by the user.

The abnormality detection procedure outputs an indication of any region of ischemia or dense vessel that has been found in the abnormality detection procedure.

The comparison circuitry 28 may compare the specified side of the brain to the side of the brain that is indicated by eye gaze or by any other data.

At stage 60, the rendering circuitry 26 updates the displayed at least one image in accordance with the re-run abnormality detection procedure of stage 58. Any abnormal region that has been found in stage 58 is highlighted in the displayed at least one image. The rendering circuitry 26 displays an indication of the side of the brain on which the abnormality detection procedure was run. The rendering circuitry 26 may also add or remove a flag 50 or further flag to indicate any inconsistency between the specified side of the brain to the side of the brain that is indicated by eye gaze or by any other data.

In the present embodiment, the abnormality detection procedure of stage 52 is run on the entire brain. At stage 56, the user specifies a side of the brain on which to perform the abnormality detection procedure. At stage 58, the abnormality detection procedure is performed for the side of the brain that is selected by the user.

In other embodiments, the abnormality detection procedure of stage 52 is run on a first side of the brain. In some embodiments, the first side of the brain is selected by the user. In some embodiments, the first side of the brain is selected automatically by the abnormality detection circuitry 29 based on the eye gaze direction determined at stage 32 or based on other data, for example other clinical symptoms. At stage 56, the user is given the option of switching to the other side of the brain. If the user chooses to switch to the other side of the brain, at stage 58 the abnormality detection circuitry 29 re-runs the abnormality detection procedure on the other side of the brain.

Two instances of the abnormality detection procedure are shown in FIG. 2 (stage 52 and stage 58). In other embodiments, any suitable number of instances of the abnormality detection procedure may be performed. For example, the clinician may alternate between performing the abnormality detection procedure on different sides of the brain. In some embodiments, the user is given the option of running the algorithm on the image without providing the algorithm with an automatically detected eye gaze direction and/or without providing the algorithm with other clinical information.

Based on clinical practice, it may be considered that it makes sense to input eye gaze direction and/or other relevant clinical information to an algorithm that is configured to automatically detect stroke signs, for example to an algorithm used in the abnormality detection procedure. However, there are several places in which errors may occur in automated detection. In some circumstances, errors may arise in an algorithm that is detecting eye gaze deviation. For example, there may be an error in detection. In some circumstances, an error may occur in clinical information, for example due to human or machine error causing incorrect reporting. The clinical information may not agree or may otherwise provide incorrect information to the automatic algorithm. Therefore, if the eye gaze detection and/or other clinical information were always to be used as input to the algorithm for detecting stroke signs, it is possible that in some cases the automatic algorithm may compute results based on incorrect information or assumptions and could thus make significant errors in its results.

By flagging inconsistencies as in the method of FIG. 2, the user may be provided with a warning of a possible error. The user may make the choice to re-run the algorithm on a selected side or on an opposite side to that already run.

The method of FIG. 2 may provide a clinical application for stroke signs detection from head scans featuring automatic eye gaze detection. The clinical application may be for stroke ischemia detection from NCCT.

The eye gaze detection may be input into a stroke signs algorithm for improved detection. The eye gaze detection may be displayed to a user. An automatic axial alignment of an imaging plane with the eye lenses may be performed to provide a quick user confirmation. For example, an aligned slice of a scan may be displayed so that the user can confirm an eye deviation detection. A flag may be raised if the eye gaze detection does not agree with the stroke signs detection or with the clinical side of the patient's symptoms. For example, a flag may be displayed if the eye gaze detection does not match at an automatic ischemia detection. A flag may be displayed if the eye gaze detection does not match at an automatic dense vessel detection. A flag may be displayed if the eye gaze detection does not match one or more clinical symptoms (if present).

The user may be allowed to rerun the automatic algorithm forcing an opposite or specific side. The automatic algorithm may ignore some or all clinical inputs.

The method of FIG. 2 may provide assistance to the user in interpreting results of the abnormality detection. The method of FIG. 2 may provide information to the user in a manner that is intuitive and easy to interpret. The user may be provided with an appropriate level of information to inform the user's clinical practice. The user may be given enough information to decide whether to accept a result of an automated abnormality detection, to re-run the automated detection and/or to review images manually to verify the automated detection.

A stroke may be an example of a serious life-threatening medical condition and may require urgent medical attention. Ischemic stroke is one example of a condition that has a limited time window in which a clinician should make a treatment decision. The sooner a patient receives correct treatment, the less damage they may be likely to sustain. In this limited time window, decisions may need to be made quickly if brain tissue is to be saved. The method described above with reference to FIG. 2 may aid the clinician in performing a rapid and accurate diagnosis.

As has been described above, the abnormality detection procedure comprises processing the volumetric NCCT data to detect one or more abnormalities, for example one or more signs of stroke.

In some embodiments, the abnormality detection procedure comprises applying a trained model to the volumetric NCCT data to identify one or more regions of abnormality. The trained model may comprise a deep learning algorithm. The trained model may comprise a neural network, for example a convolutional neural network (CNN). The trained model may comprise a U-Net. In other embodiments, the trained model may comprise any suitable form of machine learning, for example a support-vector machine (SVM) or a regression forest. The trained model may make use of features such as, for example, intensity features, gradient features and/or Gabor filters.

The trained model may be stored in data store 20 or in any suitable memory, which may be local or remote. In other embodiments, the trained model may be implemented in hardware, for example by using at least one ASIC or FPGA.

The trained model is trained to detect regions of abnormality in brain imaging data, for example to segment regions of ischemia and/or hyperdense vessels. The trained model is trained on multiple training sets of volumetric NCCT data. In some embodiments, the training sets of volumetric NCCT data have been labelled with ground truth.

In different embodiments, different methods of inputting the eye gaze into the trained model may be used.

In some embodiments, a deep learning algorithm with shared weights is trained to perform multiple tasks. The deep learning algorithm is trained using multi-task learning. The multiple tasks may include both detecting regions of abnormality and detecting an eye gaze direction. Eye gaze detection may be used to interpret other results.

In some embodiments, for example the embodiment of FIG. 2, the eye gaze is detected as a pre-processing step. The determined eye gaze direction is then used as an input for stroke sign detection.

In other embodiments, the eye gaze detection is used during post-processing of algorithm results. For example, an image that is output may be masked such that only one side of the brain is displayed.

In some embodiments, the eye gaze direction is used to modify an activation function of the trained model, for example a sigmoid or ReLU (rectified linear unit) activation function. The eye gaze direction may be used to modify one or more thresholds for each side of the brain. The application of the trained model to one side of the brain (for example, the left side) may be different from the application of the trained model to the other side of the brain (for example, the right side).

In some embodiments, the trained model comprises a self-learning model. The self-learning model continues to learn while it is in use. The self-learning model may be automatically refined over time. The self-learning model may update its internal algorithm based on its outputs.

In the embodiment of FIG. 2, eye gaze is detected and is used as an input to stroke detection. Eye gaze may be considered to be a non-brain feature that is potentially relevant to stroke. Eye gaze may be considered to be a clinical sign or symptom.

In other embodiments, other non-brain signs or symptoms may be considered. The non-brain signs or symptoms may comprise other information that may indicate that a stroke has occurred. The non-brain signs or symptoms may comprise information that may indicate a side of the brain on which the stroke occurred. Non-brain signs or symptoms on one side of the body (for example, the left side of the body) are indicative of damage to the opposite side of the brain (in this example, the right hemisphere).

In some embodiments, at least one non-brain sign or symptom is determined from the volumetric NCCT scan. In some embodiments, at least one non-brain sign or symptom is determined from a further scan of the same patient. The further scan may be obtained using any suitable modality and protocol. For example, the further scan may be a CT scan in which contrast is used.

When performing a CT scan of a region of a patient's body, it is common to first perform a three-dimensional (3D) scanogram. The 3D scanogram may have a larger field of view than the local scan of the region that is to be performed. The 3D scanogram may comprise a low-resolution scan of a larger region of the patient's body, for example the whole of the patient's body. In some embodiments, the non-brain feature or item of clinical information is determined from the 3D scanogram.

In some circumstances, an optical image of the patient may be taken during acquisition of another imaging modality, for example during CT acquisition. For example, an image of patient may be taken during an acquisition and stored with the imaging data from that acquisition. In some embodiments, the non-brain feature or item of clinical information is determined from the optical imaging during acquisition. In some embodiments, the non-brain sign or symptom is determined from other optical imaging.

The non-brain feature may be a relative angle of the patient's head on the patient's trunk (bent neck). The head on trunk angle may comprise an angle by which the patient's head deviates to the right or left. The head on trunk angle may be measured relative to a central, forward-facing position of the head. The head on trunk angle may be indicative of a laterality of stroke in a similar manner to eye gaze. The angle at which the head is positioned may be indicative of the side of the body on which the stroke has occurred.

In some embodiments, the head on trunk angle is estimated from the 3D scanogram. In some embodiments, the head on trunk angle is estimated from a CT angiography (CTA) scan. The CTA scan may include the carotid arteries, and so may include enough of the neck to estimate a head on trunk angle. In some embodiment, the head on trunk angle is estimated from optical imaging. The estimating of the head on trunk angle may use the assumption that the patient is squarely aligned with the table.

The non-brain sign or symptom may comprise a facial asymmetry or other asymmetry. In some embodiments, a facial asymmetry may be an indication that a stroke has occurred. If it can be determined which side of the face has been affected by the stroke (for example, which side is affected by drooping and/or paralysis), the facial asymmetry may provide an indication of the laterality of the stroke. The non-brain sign or symptom may comprise a tongue deviation.

In some embodiments, the non-brain sign or symptom comprises compression of laryngeal muscles. Compression of the laryngeal muscles may be a sign of dysphagia. Dysphagia is clinical symptom of stroke which may be seen on imaging.

In some embodiments, a surface of the patient is determined using the volumetric NCCT data and/or using other imaging data. For example, slice to volume reconstruction (SVR) may be used to determine a surface. The resulting surface and/or the imaging data may be automatically analyzed to determine a facial asymmetry or other asymmetry. In some embodiments, an image from an optical camera is used to determine a facial asymmetry or other asymmetry.

In some embodiments, eye muscle tension is used instead of or in addition to a determination of eye gaze based on the eyes themselves. Eye muscle tension may be used if the scan does not include the lenses of the eyes. The determining of eye muscle tension may comprise detecting and/or segmenting the extraocular muscles and identifying a compression of the extraocular muscle that is indicative of an eye gaze direction. The compression may cause the muscle to appear more dense.

In further embodiments, the non-brain signs or symptoms may be clinical signs or symptoms that are indicative of any form of brain condition, for example any suitable brain disease and/or brain trauma. The regions of abnormality that are detected in the abnormality detection procedure may be any type of abnormality associated with that brain condition. The signs or symptoms may include any type of behavior of any appropriate body part, for example a position and/or orientation and/or motion of that body part.

In the embodiments described above, an eye gaze direction is determined for a single NCCT scan. In other embodiments, eye gaze direction may be compared over multiple acquisitions. In some embodiments, an eye gaze direction that is determined for a NCCT scan is compared with an eye gaze direction that is determined for a subsequent CTA scan. A flag or other warning is generated if the eye gaze direction determined for the CTA scan is not the same as the eye gaze direction determined for the NCCT scan. In other embodiments, eye gaze direction may be compared across any number of scans of any suitable modality and/or protocol to check for consistent deviation. In further embodiments, any non-brain feature or clinical information may be compared across multiple scans.

Embodiments above describe the detection of abnormal regions of the brain for ischemic stroke. In other embodiments, methods described above may be used for hemorrhagic stroke. In further embodiments, methods described above may be used with regard to regions of any appropriate abnormality that is indicative of any appropriate brain condition, for example intracerebral hemorrhage.

The patient may be any suitable human or animal subject. References to medical may include veterinary.

In further embodiments, the signs or symptoms that are detected may be clinical signs or symptoms that are indicative of any disease or condition, which may not be a brain condition. Any suitable type of abnormality may be detected. The abnormality detection may make use of the detected signs or symptoms. Alternatively, the processing circuitry may determine whether the signs or symptoms are consistent with the abnormality.

In some embodiments, swelling may be detected and may be used, for example, to show signs of trauma. The swelling may be outside the skull, or outside another part of the body. In the head, the detection of swelling may be used to look for contrecoup injuries.

In some embodiments, detection of soft tissue oedema may be used to indicate trauma.

In some embodiments, detection of signs and symptoms may be useful if some of a clinical picture may be missing. For example we consider the case of an elderly woman with lung cancer. A radiologist is reading a scan, without complete information. The radiologist does not have the information that the patient has had a fall. In some circumstances, rib fractures may look like metastases. In the absence of the information that the patient has had a fall, there may be a reduced chance of rib fractures being correctly identified. If soft tissue oedema is identified, the soft tissue oedema may be an indication of trauma.

Lower limb oedema may be indicative of particular conditions. For example, unilateral oedema may be a prompt to look for deep vein thrombosis. Bilateral oedema may be an associated symptom of heart failure.

The non-brain signs or symptoms may comprise body temperature. Camera-based imaging may be used to obtain non-brain signs and symptoms. For example, jaundice may be detected based on optical imaging.

Many embodiments above are described with reference to a single set of medical imaging data, which may be obtained at a single time. A single determination of eye gaze direction, or of another clinical sign or symptom, may be obtained.

In further embodiments, longitudinal medical imaging data is obtained which is acquired over time, for example by taking multiple scans of the subject. The longitudinal medical imaging data may be representative of the subject at two or more times. Eye gaze direction, or another clinical sign or symptom, may be obtained for each of the times.

As mentioned above, in some embodiments eye gaze direction may be compared over multiple acquisitions. An eye gaze direction that is determined for a NCCT scan may be compared with an eye gaze direction that is determined for a subsequent CTA scan.

A sustained eye gaze deviation may be an eye gaze deviation that deviates in a consistent direction over time. A sustained eye gaze deviation may be an eye gaze deviation that deviates in a consistent direction over multiple scans. For example, it may be determined that sustained eye gaze deviation has occurred if the eye gaze direction is Left over two or more scans, or if the eye gaze direction is Right over two or more scans.

In some embodiments, the eye gaze detection circuitry 24 determines whether there is a sustained eye gaze deviation. The eye gaze detection circuitry 24 determines that there is a sustained eye gaze deviation if the eye gaze direction is Left across two successive scans, or if the eye gaze direction is Right across two successive scans. The two successive scans may comprise an NCCT scan and a CTA scan.

In other embodiments, the eye gaze detection circuitry 24 determines that there is a sustained eye gaze deviation if the direction of eye gaze is consistent as Left or Right across any suitable number of scans, for example three, four, or more scans. The eye gaze detection circuitry 24 may determine that there is sustained eye gaze deviation if the direction of eye gaze is consistent as Left or Right over a predetermined time period.

The comparison circuitry 28 may compare a side of the brain output by the abnormality detection circuitry 29 to a direction of sustained eye gaze deviation. A flag may be displayed if an inconsistency is present.

The rendering circuitry 26 may display a simplified representation of a direction of sustained eye gaze. In some embodiments, the simplified representation comprises individual representations of the eye gaze direction in multiple scans. For example, two cartoon versions of a pair of eyes may be displayed, where the first pair of eyes is representative of the eye gaze direction in the NCCT scan, and the second pair of eyes is representative of the eye gaze direction in the CTA scan.

Any suitable visual indication of sustained eye gaze deviation may be presented to the user. For example, a text indication and/or an additional graphical element may be used to indicate sustained eye gaze deviation to the user.

Certain embodiments provide a medical image processing apparatus comprising processing circuitry configured to: acquire image data including a brain of a subject and clinical information relating to brain disease of the subject, estimate an abnormal part by the brain disease based on the image data, check a consistency between the clinical information and estimation result by referring the clinical information and the estimation result. The clinical information may be information relating to behavior of a body part of the subject. The behavior of the body part may be specified based on the image data. The processing circuitry may be further configured to display reference information if the clinical information and the estimation results are inconsistent. The processing circuitry may be further configured to restrict the region of the processing to each half region of the brain of the subject if the clinical information and the estimation results are inconsistent.

Certain embodiments provide a medical imaging apparatus comprising a means of displaying images (CT) acquired for stroke (such as MPR view); a means of automatically detecting and displaying a plurality of non-brain features (possibly clinical information); a means of comparing the non-brain features with a plurality of automatically detected signs of stroke; and a means of indicating when the non-brain features and the automatically detected stroke signs do not agree.

The non-brain features may indicate laterality of stroke. The apparatus may further comprise a means of re-running the algorithm forcing detection on the opposite side or a specific side of the brain. The signs of stroke may comprise one of: ischemia, hyperdense vessel. The non-brain feature may be conjugate eye gaze deviation.

The clinically significant information may be shown via a simplified image rendition (eye cartoon). The image data within a detected eye bounding box at the appropriate plane may be displayed such that the eye deviation can be interpreted directly. The localization and alignment of eyes may be performed automatically.

The non-brain feature may be asymmetric muscle tension. The non-brain feature may be head on trunk deviation. The head on trunk deviation may be as measured in at least one of CTA, 3D scanogram, optical. The non-brain feature may be face asymmetry. The face asymmetry may be as measured in optical. Mismatch may be identified between multiple scans of same patient.

The automatically detected non-brain features may be input to the automatic detection of stroke signs. The non-brain features may be used as a direct input to the detection of signs of stroke (for example as input to a deep learning algorithm). The non-brain features may be input to a plurality of the network layers. The non-brain features may modify the activation function (for example sigmoid, ReLU, etc.) in some way. The non-brain features may be used as post-processing to aid user interpretation. The non-brain features and stroke signs detection may be combined. Both types of detection may be performed by a single deep learning algorithm, for example multi-task learning. The non-brain features may be input to some form of learning which in turn is input to the CNN.

Figure 3:
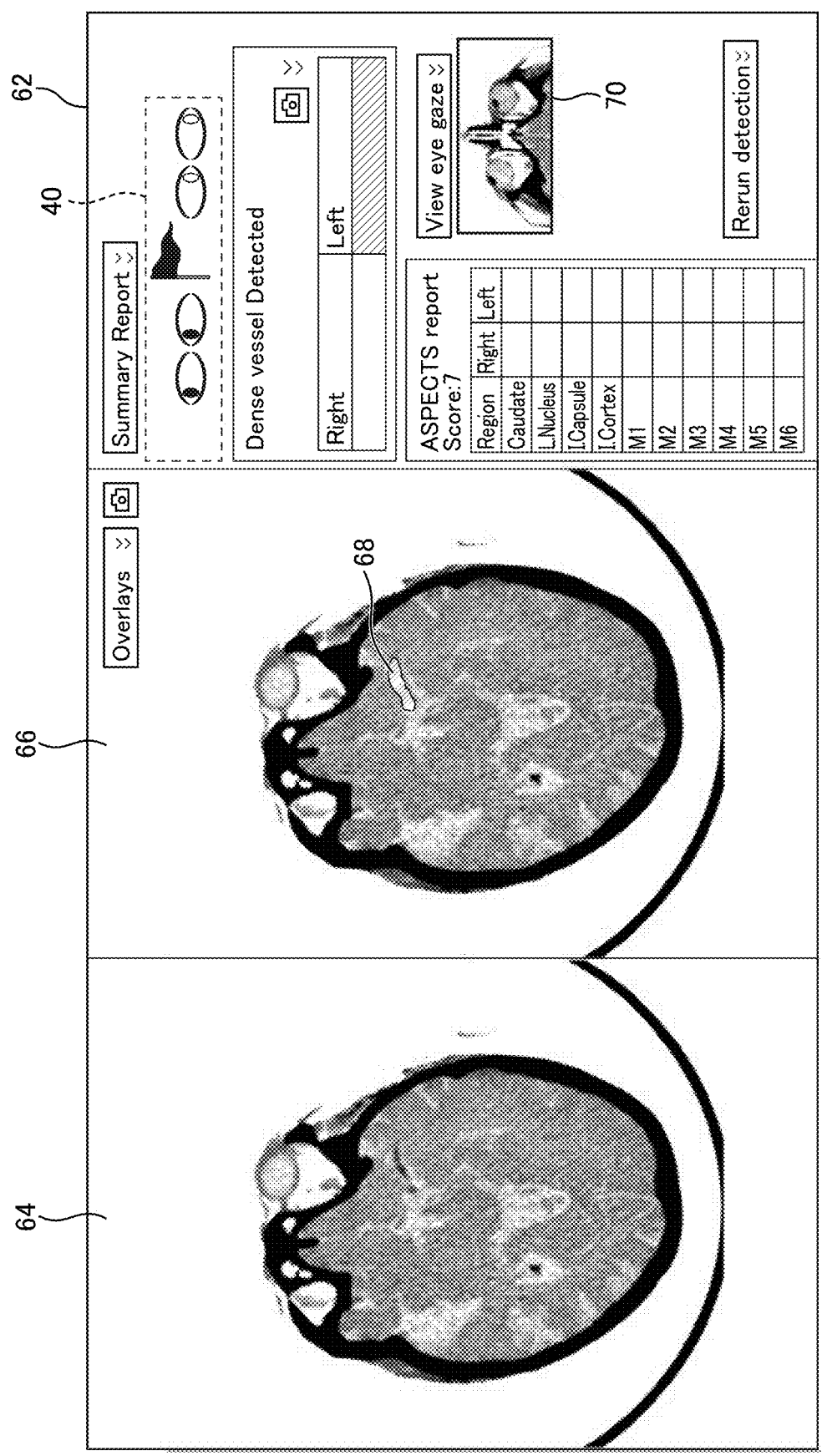
FIG. 3 is a diagram showing an exemplary screen image according to an embodiment.

FIG. 3 is a diagram showing an exemplary screen image according to a certain embodiment. The screen image 62 as given in FIG. 3 is displayed on the display device 16. The screen image 62 includes, for example, the representation 40, a CT image 64, an overlay image 66, and an eye gaze image 70. Through the screen image 62, the user can generally grasp the result of processing performed in respective stage of FIG. 2.

The CT image 64 is, for example, a section of the brain rendered by the rendering circuitry 26. More specifically, and for example, the CT image 64 shows a section of the brain from which an abnormal region has been detected.

The overlay image 66 corresponds to the CT image 64 on which a detected abnormal region 68 is overlaid. More specifically, and for example, this secondary or second CT image 66 is indicative of the abnormal region 68 on the right brain area.

The eye gaze image 70 is, for example, a portion of an imaging plane covering the lenses of the eyes, rendered by the rendering circuitry 26. More specifically, the eye gaze image 70 shows an eye region. The user can directly check the eye deviation through the eye gaze image 70.

The representation 40 in this example shows the highlighted first line drawing 42, and as such, the representation 40 indicates that the deviation of the eyes is to the left. Also, the representation 40 in this example shows the highlighted flag 50, indicating that there is mismatch between the direction of gaze determined in stage 32 and another result.

Said another result may be, for example, a position of the abnormal region detected by the CT scan, a direction of gaze input by the user, an angle of the head detected by the CTA scan, etc. Such results are each relevant to the direction of gaze determined in stage 32.

The flowchart of FIG. 2 in the foregoing description encompasses, for example, each of the flowcharts of FIGS. 4 to 6 below. The flowcharts of FIGS. 4 to 6 differ in the respect of what is to be compared to the direction of gaze.

Figure 4:
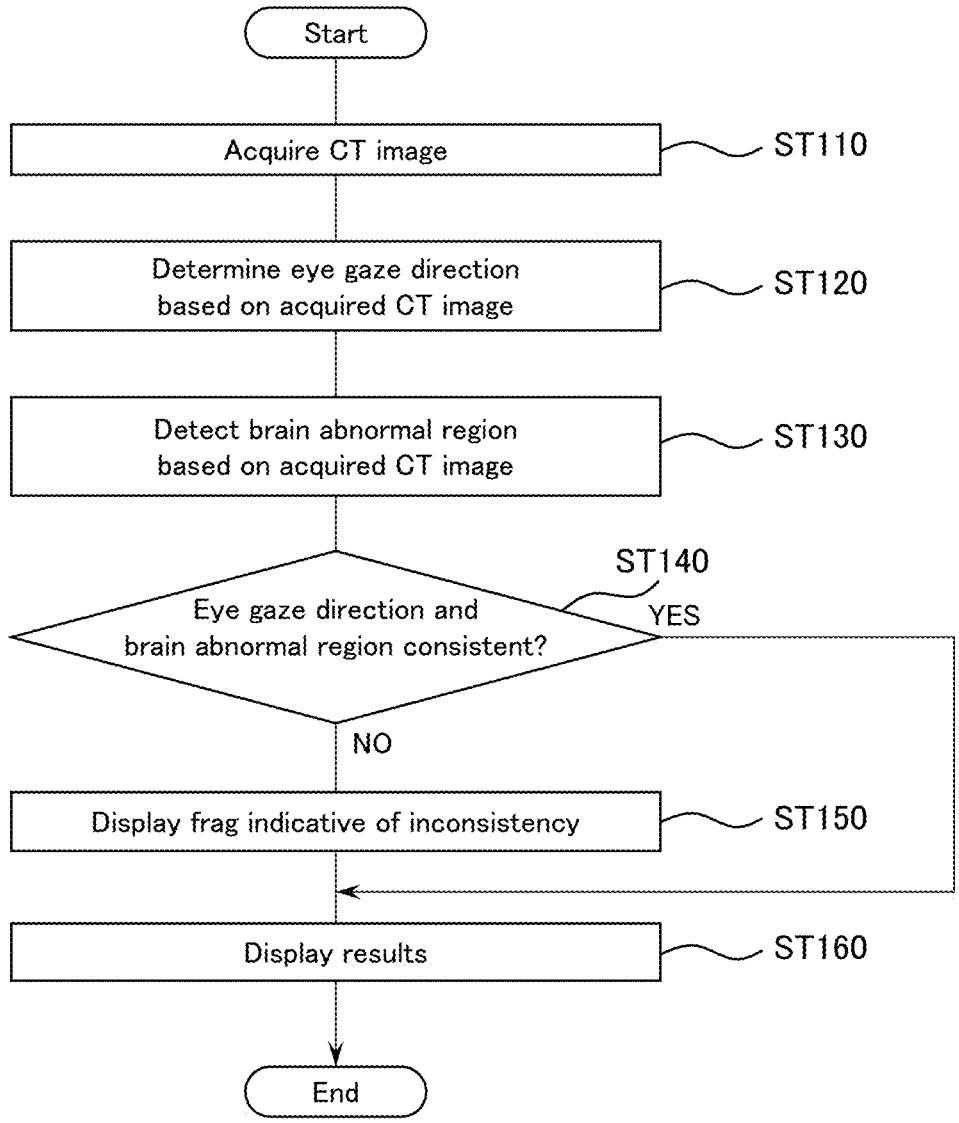
FIG. 4 is a flowchart for explaining a first concrete example according to an embodiment.

FIG. 4 is a flowchart for explaining a first concrete example according to a certain embodiment. The first concrete example assumes the instance where the direction of gaze determined from a CT image is compared to the abnormal region in the brain detected from the CT image.

At the outset of the flowchart of FIG. 4, the eye gaze detection circuitry 24 acquires a CT image obtained by the CT scanner 14 (step ST110). After acquisition of the CT image, the eye gaze detection circuitry 24 determines the direction of gaze based on the acquired CT image (step ST120). The abnormality detection circuit 29 detects the abnormal region in the brain based on the acquired CT image (step ST130).

With the direction of gaze having been determined and the abnormal region in the brain having been detected, the comparison circuitry 28 compares the direction of gaze to the abnormal region in the brain, and determines if the comparison result is indicative of consistency therebetween (step ST140). If the comparison result is not determined to be indicative of the consistency, the processing flow advances to step ST150. If the comparison result is determined to be indicative of the consistency, the processing flow advances to step ST160.

In step ST150, the rendering circuitry 26 displays a flag indicative of the inconsistency. For example, such a flag is shown in the representation 40 as in FIG. 3. In step ST160, the rendering circuitry 26 displays the results on the display device 16. Upon performing step ST160, the processing flow in the flowchart of FIG. 4 comes to the end.

Figure 5:
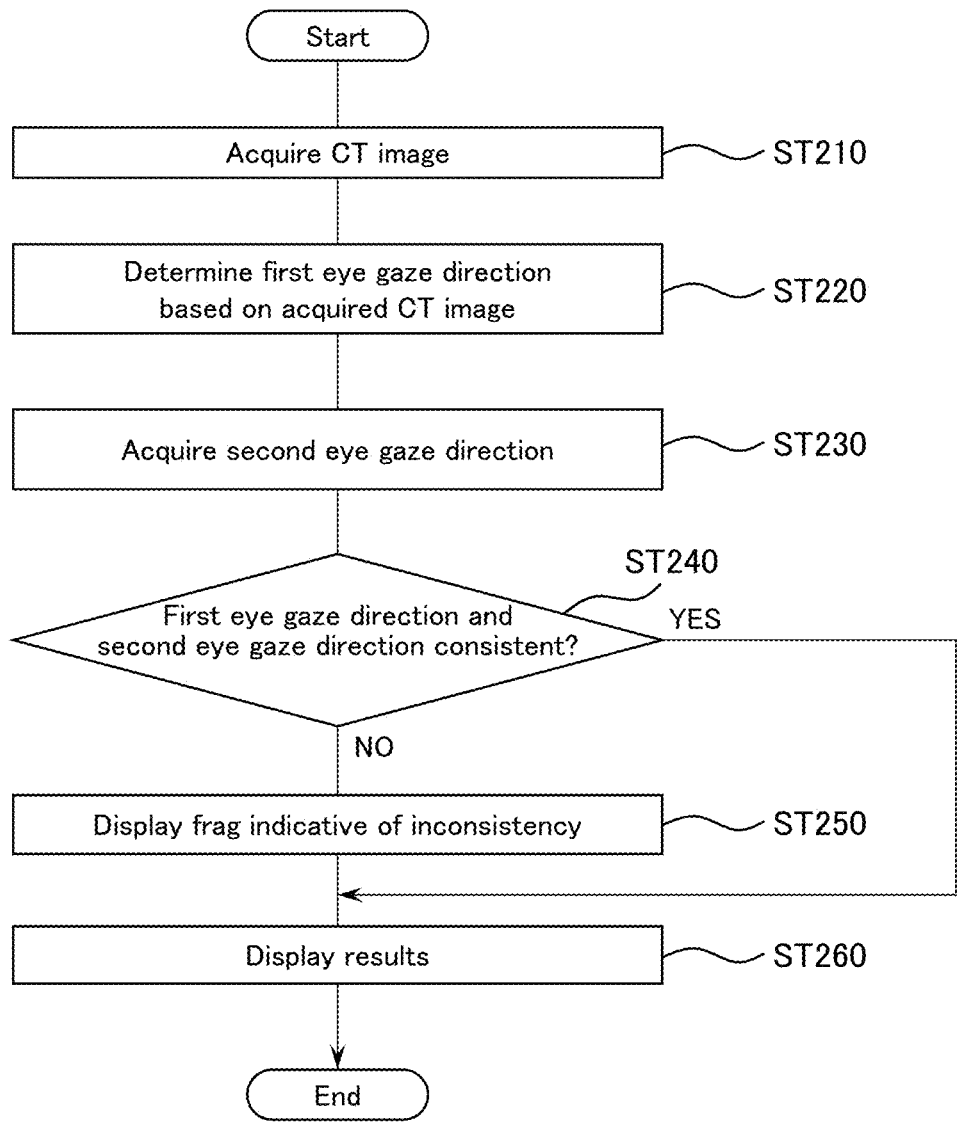
FIG. 5 is a flowchart for explaining a second concrete example according to an embodiment.

FIG. 5 is a flowchart for explaining a second concrete example according to a certain embodiment. The second concrete example assumes the instance where the direction of gaze determined from a CT image is compared to the direction of gaze determine through other method. The example of such other method may be a user inputting the direction of gaze.

In the flowchart of FIG. 5, the eye gaze detection circuitry 24 first acquires a CT image obtained by the CT scanner 14 (step ST210). After acquisition of the CT image, the eye gaze detection circuitry 24 determines a first direction of gaze based on the acquired CT image (step ST220).

The computing apparatus 12 acquires a second direction of gaze (step ST230). More specifically, the computing apparatus 12 acquires the second direction of gaze input by the user via the input device 18.

With the first direction of gaze having been determined and the second direction of gaze having been acquired, the comparison circuitry 28 compares the first direction of gaze to the second direction of gaze, and determines if the comparison result is indicative of consistency therebetween (step ST240). If the comparison result is not determined to be indicative of the consistency, the processing flow advances to step ST250. If the comparison result is determined to be indicative of the consistency, the processing flow advances to step ST260.

In step ST250, the rendering circuitry 26 displays a flag indicative of the inconsistency. For example, such a flag is shown in the representation 40 as in FIG. 3. In step ST260, the rendering circuitry 26 displays the results on the display device 16. Upon performing step ST260, the processing flow in the flowchart of FIG. 5 comes to the end.

Figure 6:
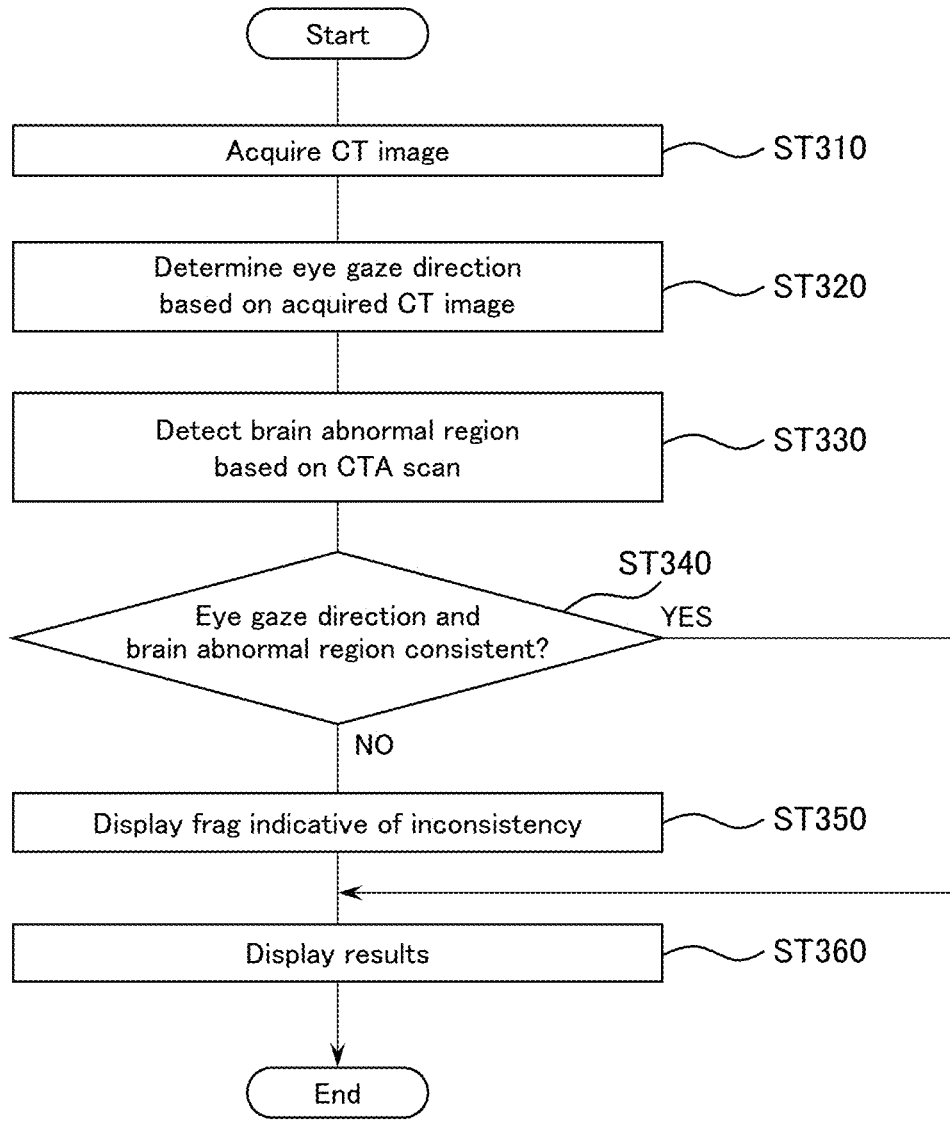
FIG. 6 is a flowchart for explaining a third concrete example according to an embodiment.

FIG. 6 is a flowchart for explaining a third concrete example according to a certain embodiment. The third concrete example assumes the instance where the direction of gaze determined from a CT image is compared to the abnormal region in the brain detected by the CTA scan.

In the flowchart of FIG. 6, the eye gaze detection circuitry 24 first acquires a CT image obtained by the CT scanner 14 (step ST310). After acquisition of the CT image, the eye gaze detection circuitry 24 determines a direction of gaze based on the acquired CT image (step ST320).

The computing apparatus 12 detects the abnormal region in the brain based on the CTA scan (step ST330). More specifically, the computing apparatus 12 detects the abnormal region in the brain from a CTA scan image obtained by the CT scanner 14.

With the direction of gaze having been determined and the abnormal region in the brain having been detected, the comparison circuitry 28 compares the direction of gaze to the abnormal region in the brain, and determines if the comparison result is indicative of consistency therebetween (step ST340). If the comparison result is not determined to be indicative of the consistency, the processing flow advances to step ST350. If the comparison result is determined to be indicative of the consistency, the processing flow advances to step ST360.

In step ST350, the rendering circuitry 26 displays a flag indicative of the inconsistency. In step ST360, the rendering circuitry 26 displays the results on the display device 16. Upon performing step ST360, the processing flow in the flowchart of FIG. 6 comes to the end.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus, comprising:
processing circuitry configured to:
obtain image data representative of a brain of a subject;
obtain data representing a clinical sign or symptom of the subject, the clinical sign or symptom being indicative of a side of the brain in which a brain condition occurs;
process the image data to obtain an estimation of an abnormality in the brain of the subject including determining a side of the brain in which the abnormality is present; and
determine whether the estimation of the abnormality is consistent with the data representing the clinical sign or symptom including determining that an inconsistency is present if the side of the brain in which the brain condition occurs as indicated by the data representing the clinical sign or symptom is not the same as the side of the brain in which the abnormality is present as determined by processing the image data to obtain the estimation of the abnormality.

2. The apparatus according to claim 1,
wherein the brain condition is stroke, and
wherein the clinical sign or symptom is indicative of a laterality of the stroke.

3. The apparatus according to claim 1, wherein the clinical sign or symptom comprises at least one of a behavior of a body part, a position of a body part, an orientation of a body part, and a motion of a body part.

4. The apparatus according to claim 1, wherein the clinical sign or symptom comprises at least one of an eye gaze direction, an angle of eye gaze, an asymmetric muscle tension, an angle of head on trunk, a face asymmetry, and a tongue deviation.

5. The apparatus according to claim 1, wherein the clinical sign or symptom comprises a sustained eye deviation.

6. The apparatus according to claim 1, wherein the clinical sign or symptom comprises an eye deviation occurring in two or more scans and/or at two or more times.

7. The apparatus according to claim 1,
wherein the image data comprises data acquired at a plurality of times and/or as a plurality of scans, and
wherein the processing circuitry is configured to obtain the data representing the clinical sign or symptom at each of the plurality of times and/or in each of the plurality of scans.

8. The apparatus according to claim 1, wherein
the processing circuitry is further configured to process the image data to obtain the data representing the clinical sign or symptom, and/or
the processing circuitry is further configured to process further image data to obtain the data representing the clinical sign or symptom.

9. The apparatus according to claim 1, wherein the processing circuitry is further configured to display reference information if the inconsistency is present.

10. The apparatus according to claim 1, wherein the processing circuitry is further configured to:
display an image rendered from at least part of the image data, and
display on the rendered image an indication of at least one region of abnormality based on the estimation of the abnormality.

11. The apparatus according to claim 1,
wherein the processing circuitry is further configured to receive a selection of a side of the brain made in response to a determination that the inconsistency is present; and
wherein the processing circuitry is further configured to process the image data with the processing restricted to the selected side of the brain to obtain an estimation of an abnormality in the selected side of the brain.

12. The apparatus according to claim 1, wherein the processing circuitry is further configured to display a simplified representation of the clinical sign or symptom.

13. The apparatus according to claim 12, wherein
the processing circuitry is configured to obtain respective data representing the clinical sign or symptom of the subject at each of a plurality of times and/or in each of a plurality of scans, and
the simplified representation is representative of the clinical sign or symptom at each of the plurality of times and/or plurality of scans.

14. The apparatus according to claim 1, wherein the processing circuitry is configured to:
select a part of the image data that is related to the clinical sign or symptom, and
display the selected part of the image data.

15. The apparatus according to claim 1, wherein the abnormality comprises at least one of a region of ischemia and a region of hyperdense vessel.

16. The apparatus according to claim 1, wherein the processing circuitry is configured to:
compare the data representing the clinical sign or symptom to previously-obtained data relating to the clinical sign or symptom, and
identify whether there is a mismatch between the data and the previously-obtained data.

17. The apparatus according to claim 1, wherein the processing of the image data is based on the data representing the clinical sign or symptom.

18. The apparatus according to claim 1, wherein the processing of the image data comprises applying a trained model.

19. The apparatus according to claim 18, wherein the data representing the clinical sign or symptom is used as an input to the trained model.

20. The apparatus according to claim 19, wherein at least one of a) to c):
a) the data representing the clinical sign or symptom is input to a plurality of network layers of the trained model;
b) the data representing the clinical sign or symptom is used to modify an activation function of the trained model; and
c) a single trained model is used to process the image data to both obtain the data representing the clinical sign or symptom and obtain the estimation of the abnormality.

21. The apparatus according to claim 1, wherein the data representing the clinical sign or symptom of the subject comprises data input by a user.

22. A medical image processing method comprising:
obtaining image data representative of a brain of a subject;
obtaining data representing a clinical sign or symptom of the subject, the clinical sign or symptom being indicative of a side of the brain in which a brain condition occurs;
processing the image data to obtain an estimation of an abnormality in the brain of the subject including determining a side of the brain in which the abnormality is present; and
determining whether the estimation of the abnormality is consistent with the data representing the clinical sign or symptom including determining that an inconsistency is present if the side of the brain in which the brain condition occurs as indicated by the data representing the clinical sign or symptom is not the same as the side of the brain in which the abnormality is present as determined by processing the image data to obtain the estimation of the abnormality.

23. A non-transitory computer program product storing computer-readable instructions that are executable to:
obtain image data representative of a brain of a subject;
obtain data representing a clinical sign or symptom of the subject, the clinical sign or symptom being indicative of a side of the brain in which a brain condition occurs;
process the image data to obtain an estimation of an abnormality in the brain of the subject including determining a side of the brain in which the abnormality is present; and
determine whether the estimation of the abnormality is consistent with the data representing the clinical sign or symptom including determining that an inconsistency is present if the side of the brain in which the brain condition occurs as indicated by the data representing the clinical sign or symptom is not the same as the side of the brain in which the abnormality is present as determined by processing the image data to obtain the estimation of the abnormality.

* * * * *